United States Patent [19]

Grosskinsky et al.

[11] Patent Number: 4,551,318

[45] Date of Patent: Nov. 5, 1985

[54] STABILIZED SOLUTIONS OF HYDROXYLAMINE OR ITS SALTS IN WATER OR ALCOHOLS, AND THEIR PREPARATION

[75] Inventors: Otto-Alfred Grosskinsky; Elmar Frommer; Josef Ritz, all of Ludwigshafen; Erwin Thomas, Freinsheim; Franz-Josef Weiss, Neuhofen, all of Fed. Rep. of Germany

[73] Assignee: BASF Aktiengesellschaft, Fed. Rep. of Germany

[21] Appl. No.: 685,257

[22] Filed: Dec. 24, 1984

[30] Foreign Application Priority Data

Dec. 28, 1983 [DE] Fed. Rep. of Germany ....... 3347260

[51] Int. Cl.$^4$ ............................................. C01B 21/20
[52] U.S. Cl. .................................. 423/265; 210/750; 423/387
[58] Field of Search .................. 423/265, 377, 378; 210/750

[56] References Cited

U.S. PATENT DOCUMENTS

| | | | |
|---|---|---|---|
| 3,145,082 | 8/1964 | Rausch et al. | 423/387 |
| 3,480,391 | 11/1969 | Carlos | 423/387 |
| 3,480,392 | 11/1969 | Carlos | 423/387 |
| 3,544,270 | 12/1970 | Carlos | 423/387 |

FOREIGN PATENT DOCUMENTS

| | | | |
|---|---|---|---|
| 100908 | 6/1982 | Japan | 423/265 |
| 69844 | 4/1983 | Japan | 423/387 |
| 69843 | 4/1983 | Japan | 423/387 |
| 69841 | 4/1983 | Japan | 423/387 |
| 69842 | 4/1983 | Japan | 423/387 |
| 7703020 | 9/1978 | Netherlands | 423/265 |

*Primary Examiner*—John Doll
*Assistant Examiner*—Wayne A. Langel
*Attorney, Agent, or Firm*—Keil & Weinkauf

[57] ABSTRACT

Stabilized solutions of hydroxylamine or its salts, containing anthocyans of the formula

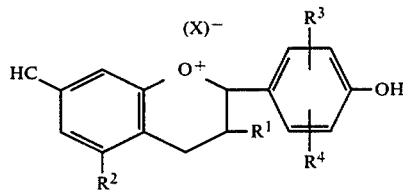

where $R^1$, $R^2$, $R^3$ and $R^4$ are each hydrogen, hydroxyl or $C_1$–$C_4$-alkoxy and X is an anion of a strong mineral acid, and their preparation.

5 Claims, No Drawings

STABILIZED SOLUTIONS OF HYDROXYLAMINE OR ITS SALTS IN WATER OR ALCOHOLS, AND THEIR PREPARATION

Solutions of hydroxylammonium salts decompose slowly at room temperature and more rapidly at elevated temperatures, this behavior being more pronounced in the case of solutions of free hydroxylamine. There has been no lack of attempts to stabilize solutions of hydroxylamine and its salts in order to achieve a longer shelf life. For example, according to U.S. Pat. No. 3,544,270, urea derivatives are used as stabilizers. U.S. Pat. No. 3,480,391 furthermore describes amidoximes for stabilizing hydroxylamine solutions, while U.S. Pat. No. 3,480,392 discloses that hydroxamic acids are suitable for this purpose. Furthermore, U.S. Pat. No. 3,145,082 discloses the use of chelate-forming agents, such as sodium ethylenediaminetetraacetate, as stabilizers. The stabilizers used to date are unsatisfactory.

It is an object of the present invention to provide stabilized solutions of hydroxylamine or its salts which are stable over a prolonged period and in which, in particular, the decomposition of free hydroxylamine is minimized.

We have found that this object is achieved by stabilized solutions of hydroxylamine or its salts in water or alcohols, which contain anthocyans of the formula

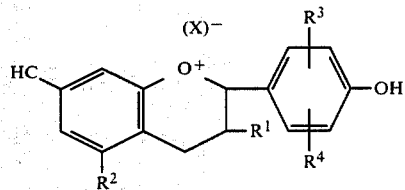

where $R^1$, $R^2$, $R^3$ and $R^4$ are each hydrogen, hydroxyl or $C_1$–$C_4$-alkoxy and X is an anion of a strong mineral acid.

The present invention furthermore relates to a process for the preparation of stabilized solutions of hydroxylamine or its salt by the addition of stabilizers, wherein the molecular oxygen dissolved in the solution to be stabilized is removed from this solution by treatment with nitrogen which is free of molecular oxygen, and an anthocyan of the formula I is then added.

The solutions of hydroxylamine or its salts which have been stabilized according to the invention have the advantage that they are stable over a longer period than prior art solutions, and in particular the decomposition of free hydroxylamine is reduced to a minimum.

According to the invention, a solution of hydroxylamine or one of its salts in water or an alcohol eg. a $C_1$–$C_4$-alkanol, is used as the starting material. Examples of suitable salts of hydroxylamine are those with a strong mineral acid, such as sulfuric acid, nitric acid or hydrochloric acid, or those with fatty acids, eg. acetic acid or propionic acid. Because of the difference in solubilities, hydroxylamine is preferably in the form of a solution in water or an alcohol, whereas its salts are preferably present as aqueous solutions. The content of hydroxylamine or its salts is, as a rule, from 10 to 70% by weight, and the hydroxylamine solutions used generally have a pH of from 8 to 11. Particularly preferably, aqueous hydroxylamine solutions are used as starting materials.

The stabilizers used are anthocyans of the formula

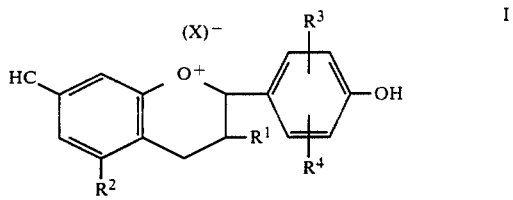

where $R^1$, $R^2$, $R^3$ and $R^4$ are each hydrogen, hydroxyl or $C_1$–$C_4$-alkoxy and X is an anion of a strong mineral acid. X is preferably a chloride or sulfate anion. In particularly preferred anthocyans of the formula I, $R^1$, $R^2$, $R^3$ and $R^4$ are each hydrogen, hydroxyl or methoxy and X is a chloride anion. The anthocyans can also be present in the form of glycosides. Suitable anthocyans are described in, for example, Angew. Chem. 68 (1956), 110 and 111, useful compounds being apigenin, pelargonidin, cyanidin, delphinidin, peonidin, petunidin and malvidin.

Advantageously, the anthocyans of the formula I are used in amounts of from 0.005 to 1, in particular from 0.01 to 0.1, % by weight, based on the solution to be stabilized. The presence of polyhydroxybenzenes, in particular pyrogallol, in addition has also proven useful, the polyhydroxybenzenes advantageously being added in amounts of from 0.005 to 0.1% by weight, based on the solution to be stabilized. It is noteworthy that the combined use of anthocyans of the formula I and polyhydroxybenzenes results in a synergistic effect.

Stabilized solutions of hydroxylamine or its salts in water or in alcohols are prepared, according to the invention, by a method in which the molecular oxygen dissolved in the solution to be stabilized is first displaced from this solution by treatment with nitrogen which is free of molecular oxygen. This is achieved by, for example, passing oxygen-free nitrogen through the solution to be stabilized, for example for from 5 to 10 minutes. The nitrogen used for this purpose advantageously contains less than 2 ppm of molecular oxygen. Anthocyans of the formula I and, if required, hydroxybenzenes are then added, and are dissolved in the said solution, the temperature advantageously being kept at from 5° to 40° C. during this procedure. It is also possible to add the stabilizers in the form of solutions to the solution to be stabilized.

It is of course advantageous if the solution to be stabilized is prevented from becoming contaminated with heavy metals, in particular copper or noble metals, since these catalyze decomposition of hydroxylamine. It is also advantageous to exclude high-energy radiation by means of suitably colored glass containers, and to store the stabilized solutions at <40° C., for example at from 5° to 20° C.

Stabilized solutions of hydroxylamine or its salts are useful for the preparation of oximes.

The Example which follows illustrates the subject of the invention.

EXAMPLE

An aqueous solution of hydroxylamine is flushed with oxygen-free nitrogen at 20° C. for 10 minutes, after which the stabilizer is added. The concentration of hydroxylamine, the type and amount of the stabilizer added and the results achieved as a function of time and temperature are shown in the Table below.

TABLE

| Stabilizer | °C. | | | | |
|---|---|---|---|---|---|
| 50 ppm of | 5 | 0 | 743 | 1198 | Hours |
| cyanidin | | 110.88 | 110.73 | 110.50 | g/l of $NH_2OH$ |
| 50 ppm of | 20 | 0 | 404 | 1195 | Hours |
| cyanidin | | 110.25 | 109.65 | 109.39 | g/l of $NH_2OH$ |
| 50 ppm of | 40 | 0 | 359 | 1194 | Hours |
| cyanidin | | 110.25 | 109.70 | 108.67 | g/l of $NH_2OH$ |

We claim:

1. A stabilized solution of hydroxylamine or its salts in water or an alcohol, which contains an anthocyan of the formula

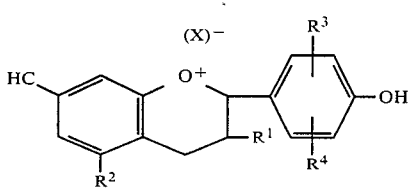

where $R^1$, $R^2$, $R^3$ and $R^4$ are each hydrogen, hydroxyl or $C_1$–$C_4$-alkoxy and X is an anion of a strong mineral acid.

2. A stabilized solution as claimed in claim 1, which contains an anthocyan of the formula I, where $R^1$, $R^2$, $R^3$ and $R^4$ are each hydrogen, hydroxyl or methoxy and X is a chloride anion.

3. A stabilized solution as claimed in claim 1, which contains from 0.005 to 1% by weight, based on the amount of the solution to be stabilized, of an anthocyan of the formula I.

4. A stabilized solution as claimed in claim 1, which additionally contains pyrogallol.

5. A process for the preparation of a stabilized solution of hydroxylamine or its salts in water or an alcohol, wherein the molecular oxygen dissolved in the solution to be stabilized is removed from the solution by treatment with nitrogen which is free of molecular oxygen, and an anthocyan of the formula I as set forth in claim 1 is then added.

* * * * *